(12) United States Patent
Morgan et al.

(10) Patent No.: US 10,624,685 B2
(45) Date of Patent: Apr. 21, 2020

(54) DEVICE FOR IMPLANTING COMPRESSION PLATE WITHIN A BODY

(71) Applicant: Arthrex, Inc., Naples, FL (US)

(72) Inventors: Dan Morgan, Salem, MA (US);
Matthew Palmer, Medford, MA (US);
Matthew Fonte, Concord, MA (US);
Robert Devaney, Auburndale, MA (US); Zachary Day, Naples, FL (US);
Chris Powell, Naples, FL (US)

(73) Assignee: Arthrex, Inc., Naples, FL (US)

( * ) Notice: Subject to any disclaimer, the term of this patent is extended or adjusted under 35 U.S.C. 154(b) by 320 days.

(21) Appl. No.: 15/632,655

(22) Filed: Jun. 26, 2017

(65) Prior Publication Data

US 2017/0367741 A1 Dec. 28, 2017

Related U.S. Application Data

(60) Provisional application No. 62/354,851, filed on Jun. 27, 2016.

(51) Int. Cl.
| | |
|---|---|
| *A61B 17/66* | (2006.01) |
| *A61B 17/80* | (2006.01) |
| *A61B 17/88* | (2006.01) |
| *A61B 17/68* | (2006.01) |

(52) U.S. Cl.
CPC ...... *A61B 17/8019* (2013.01); *A61B 17/8004* (2013.01); *A61B 17/808* (2013.01); *A61B 17/8869* (2013.01); *A61B 2017/681* (2013.01)

(58) Field of Classification Search
CPC combination set(s) only.
See application file for complete search history.

(56) References Cited

U.S. PATENT DOCUMENTS

2017/0100163 A1* 4/2017 Palmer ............... A61B 17/7225

* cited by examiner

*Primary Examiner* — Sameh R Boles
(74) *Attorney, Agent, or Firm* — Carlson, Gaskey & Olds, P.C.

(57) ABSTRACT

A delivery device delivers a compression plate to a fracture line in a bone. The delivery device includes a body that retains the compression plate in a strained condition, the body including a proximal end, a distal end, and a first beam. The delivery device also includes a cover plate attached to and moveable relative to the body, the cover plate including a second beam. A space is defined between the first beam and the second beam that receives the compression plate. The delivery device also includes a compression clip that retains the compression plate in the space.

13 Claims, 10 Drawing Sheets

FIG.13a TOP VIEW — PLATE SCREWED ONTO BONE — CONSTRAINT RELEASED BRIDGE ALLOWED TO EXPAND

FIG.13b SIDE VIEW — PLATE SCREWED ONTO BONE — CONSTRAINT RELEASED BRIDGE ALLOWED TO EXPAND

FIG.14a PLATE SCREWED ONTO BONE

DEVICE FOR IMPLANTING COMPRESSION PLATE WITHIN A BODY

REFERENCE TO PENDING PRIOR PATENT APPLICATION

This patent application claims priority to and the benefit of prior U.S. Provisional Patent Application Ser. No. 62/354,851, filed Jun. 27, 2016, the entire disclosure of which is hereby incorporated by reference.

FIELD OF THE INVENTION

The present invention relates to a device for implanting plates that generate, apply and maintain compression to a site in a human or animal body to facilitate healing of diseased or damaged tissue. The invention finds particular utility in the field of orthopedics and specifically for reducing fractures and maintaining compression between bone fragments. While the invention has application throughout the body, its utility will be illustrated herein in the context of the repair of fractured or displaced bone tissue, such as during a Calcaneal-Cuboid Arthrodesis, Metatarsal Shortening and/or Distal Radius Fixation. The present invention also finds utility as a device for implanting a cervical compression plate, and/or other spinal compression plates.

BACKGROUND OF THE INVENTION

In the field of orthopedic surgery, it is common to rejoin broken bones. The success of a surgical procedure often depends on the ability to reapproximate the bone fragments, the amount of compression achieved between the bone fragments, and the ability to sustain that compression over a period of time. If the surgeon is unable to bring the bone fragments into close contact, a gap will exist between the bone fragments, and the bone tissue will need to fill the gap before complete healing can occur. Furthermore, gaps between bone fragments that are too large allow motion to occur between the bone fragments, disrupting the healing tissue, and thus slowing the healing process. Optimal healing requires that the bone fragments be in close contact with each other and for a compressive load to be applied and maintained between the bone fragments. Compressive strain between bone fragments has been found to accelerate the healing process in accordance with Wolf's Law.

Broken bones can be rejoined using plates. The plates are formed from a sheet or ribbon of material with a plurality of holes formed therein. The plates are typically manufactured from either stainless steel alloys or titanium alloys. The plates are placed adjacent to a fracture so that the plate spans the fracture line, and then screws are inserted through holes in the plate and into the bone fragments on either side of the fracture site to stabilize the bone fragments relative to one another.

While these plates are designed to stabilize a fracture, they do not always succeed in generating a compressive load between the bone fragments. It is widely reported that the compressive load of the plates dissipates rapidly as the bone relaxes and remodels around the screws which hold the plate to the bone.

There exists a clinical need for new and improved compression plates which are able to bring bone fragments into close proximity with each other, generate a compressive load, and maintain the compressive load for a prolonged period of time during healing. Furthermore, there exists a clinical need for devices that are capable of implanting compression plates and allowing them to generate, apply, and maintain compression between bone fragments.

SUMMARY OF THE INVENTION

In one example, a delivery device delivers a compression plate to a fracture line in a bone. The delivery device includes a body that retains a compression plate in a strained condition. The body includes a proximal end, a distal end, a first beam, a cavity, and a recess. A cover plate is attached at the proximal end of the body and moveable relative to the body. The cover plate includes a second beam. The cover plate is received in the recess of the body. A space is defined between the first beam and the second beam that receives the compression plate. A compression clip retains the compression plate in the space in the strained condition and prevents the compression plate from returning to an unstrained condition. The compression clip includes an upper portion and two side portions that are substantially perpendicular to the upper portion. The upper portion includes an opening, and the cover plate can move relative to the compression plate at the distal end of the body to allow the compression plate to release from the delivery device. A male threaded rod includes a head and a male stem having male threads. The male threads are located at one end region of the male stem and the head is located at an opposing end region of the male stem. The head is located proximate to the distal end of the body and in an area defined by the upper portion and the two side portions of the compression clip. The male stem extends from the head, through the opening of the compression clip, and the through the body of the delivery device. A female threaded feature includes a knob and a female stem having a passage with female threads. The knob is located at one end region of the female stem. The female threads are located at an opposing end region of the female stem. The male threads of the male threaded rod engage the female threads of the female threaded feature. Rotation of the knob moves the male stem and thereby the head axially towards the proximal end of the body. The head contacts the upper portion of the compression clip to move the compression clip towards the proximal end of the body of the delivery device to release the compression clip. When the compression clip is received in a cavity of the body, the cover plate can move away from the compression plate at the distal end of the body to allow the compression plate to release from the delivery device.

In another example, a delivery device delivers a compression plate to a fracture line in a bone. The delivery device includes a body that retains a compression plate in a strained condition. The body includes a proximal end, a distal end, and a first beam. A cover plate is attached to and moveable relative to the body. The cover plate includes a second beam. A space is defined between the first beam and the second beam that receives the compression plate. A compression clip retains the compression plate in the space.

In another embodiment according to any of the previous embodiments, the compression clip includes an upper portion and two side portions that are substantially perpendicular to the upper portion. The upper portion includes an opening.

In another embodiment according to any of the previous embodiments, the first beam includes a first chamfered portion and the second beam includes a second chamfered portion. The first chamfered portion and the second chamfered portion are located on a proximal portion of the first beam and the second beam, respectively.

In another embodiment according to any of the previous embodiments, the cover plate is attached near or at the proximal end of the body and, when the compression clip is received in a cavity of the body, the cover plate can move away from the compression plate at the distal end of the body to allow the compression plate to release from the delivery device.

In another embodiment according to any of the previous embodiments, the delivery device includes a male threaded rod and a female threaded feature. The male threaded rod includes a head and a male stem having male threads. The male threads are located at one end of the male stem and the head is located at an opposing end of the male stem. The head is located proximate to the distal end of the body and in an area defined by the upper portion and the two side portions of the compression clip. The male stem extends from the head, through the opening of the compression clip, and the through the body of the delivery device. The female threaded feature includes a knob and a female stem having a passage with female threads. The knob is located at one end region of the female stem, and the female threads are located at an opposing end region of the female stem.

In another embodiment according to any of the previous embodiments, the male threads of the male threaded rod engage the female threads of the female threaded feature. Rotation of the knob moves the male stem and thereby the head axially towards the proximal end of the body. The head contacts the upper portion of the compression clip to move the compression clip towards the proximal end of the body of the delivery device to release the compression clip.

In another embodiment according to any of the previous embodiments, when the compression clip is received in a cavity of the body, the cover plate can move away from the compression plate at the distal end of the body to release the compression plate from the delivery device In another embodiment according to any of the previous embodiments, the compression clip locks the cover plate relative to the body.

In another embodiment according to any of the previous embodiments, the first beam and the second beam are at the distal end of the body.

In another embodiment according to any of the previous embodiments, the body includes a recess, and the cover plate is received in the recess of the body.

In another embodiment according to any of the previous embodiments, the compression plate includes an elastic bridge member disposed on both sides of a center line. First and second opposing regions each comprise an opening and are connected by the elastic bridge member. The elastic bridge member is bowed outwardly relative to the center line when in an unstrained condition. The compression plate has a more linear configuration when the compression plate is in the strained condition.

In another embodiment according to any of the previous embodiments, the openings in the first and second opposing regions are separated by a first distance when the compression plate is in the unstrained condition. The openings in the first and second opposing regions are separated by a second distance when the compression plate is in the strained condition, and the second distance is greater than the first distance.

In another example, a method of repairing a fracture line in a bone includes loading a compression plate between a body and a cover plate of a delivery device to position the compression plate in the strained condition. The compression plate is placed over the fracture line. A compression clip is axially moved away from the compression plate. The cover plate is released from the body to allow the cover plate to move relative to the body. The compression plate is released from the delivery device.

In another embodiment according to any of the previous embodiments, the method includes drilling holes through openings in the compression plate. Threaded fasteners are advanced through the openings and into the bone fragments to secure the compression plate to the bone fragments. The delivery device is removed. Compression is generated and maintained across the fracture line as the compression plate tries to return to the unstrained condition.

In another example, a delivery device delivers a compression plate to a fracture line in a bone. The delivery device includes a body that retains a compression plate in a recess in a strained condition. The body includes a first portion and a second portion defining the recess therebetween. The first portion and the second portion are moveable relative to each other to change a dimension of the recess to compress the compression plate from an unstrained condition to the strained condition. A threaded fastener is turned to move the first portion and the second portion towards each other and reduce the dimension of the recess and compression the compression plate from the unstrained condition to the strained condition. An alignment feature that aligns the first portion and the second portion relative to each other.

In another embodiment according to any of the previous embodiments, the first portion and the second portion each include a groove to receive a portion of the compression plate.

In another embodiment according to any of the previous embodiments, the first portion and the second portion each include a surface that acts as a stop to prevent movement of the first portion and the second portion towards each other.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION

Figure 1:
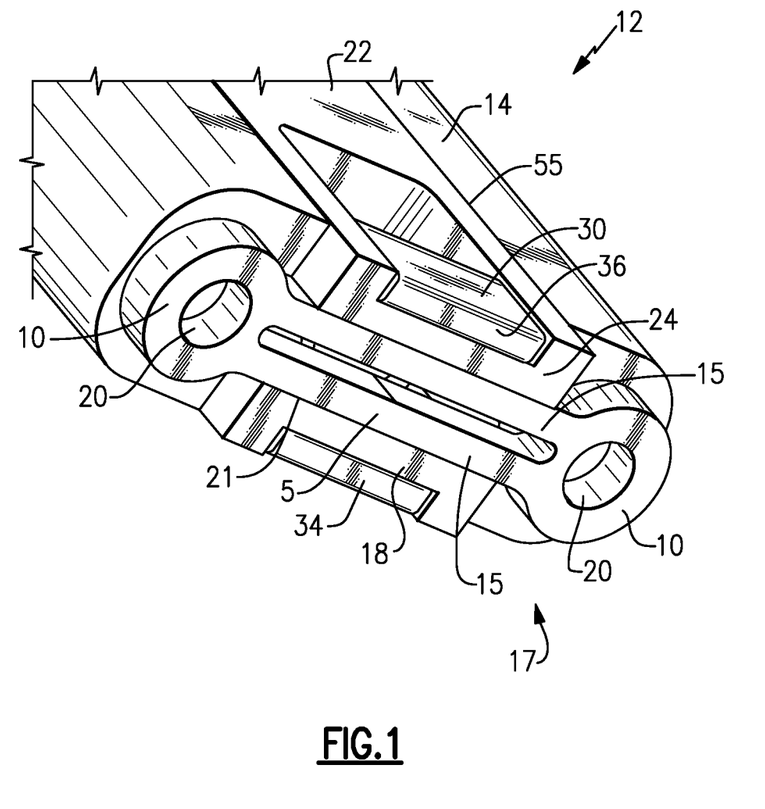
FIG. 1 illustrates a schematic view of a distal end of a body of a delivery device that delivers a compression plate to a fracture line.

As shown in FIG. 1, a delivery device 12 delivers a compression plate 5 that brings bone fragments 305 (shown in FIGS. 10a to 14b) into close proximity with each other, generates a compressive load, and maintains the compressive load for a prolonged period of time while healing occurs. The compression plate 5 maintains more uniform compression between cortical bone and cancellous bone of the bone fragments to aid in fracture healing.

The delivery device 12 includes a body 14 that holds the compression plate 5 in a strained condition (a biased condition that has a more linear configuration). The body 14 includes a proximal end 13 and a distal end 17. A distal end 17 of the body 14 includes a beam 18. A cover plate 22 is received in a recess 55 of the body 14 and can cantilever outwardly with respect to the distal end 17 of the body 14 of the delivery device 12. A beam 24 is located at a bottom of the cover plate 22. A space 21 is defined at the distal end 17 of the delivery device 12 between the beam 18 of the body 14 and the beam 24 of the cover plate 22, and the space 21 receives the compression plate 5.

Figure 2:
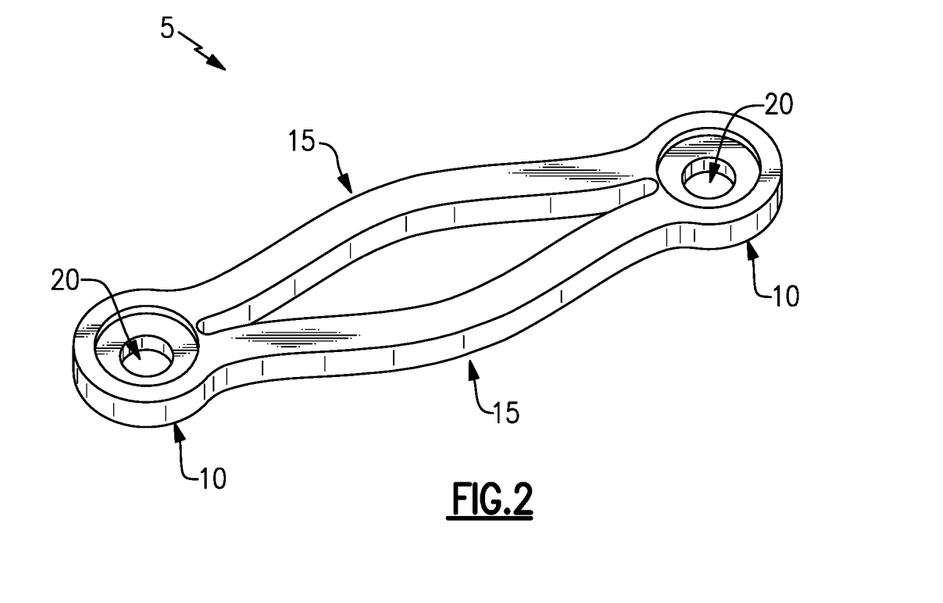
FIG. 2 is a schematic view of the compression plate in an unstrained condition.

FIG. 2 shows the compression plate 5 in an unstrained condition (an unbiased condition). The compression plate 5 brings the bone fragments 305 into close proximity with each other, generating a compressive load across the fracture line (i.e., between the cortical bone and the cancellous bone of the bone fragments 305) and maintaining the compressive load for a prolonged period of time during healing.

The compression plate 5 is manufactured from a single piece of shape memory material which is capable of exhibiting superelasticity and/or a temperature-induced shape change. The shape memory material may be a metal alloy (e.g., Nitinol) or a polymer (e.g., appropriately processed PEEK). The compression plate 5 includes two opposing regions 10 joined together by a pair of elastic bridge members 15. At least one opening 20 is formed in each of the two opposing regions 10 for receiving threaded fixation screws 120 (shown in FIGS. 10a to 14b).

The openings 20 may have a countersunk feature (e.g., a bore-counterbore configuration) to allow heads of the threaded fixation screws 120 to sit substantially flat with a top surface of the compression plate 5. Additionally, the openings 20 may be threaded to allow for positive engagement between the openings 20 and the threaded fixation screws 120. In the unstrained condition, the elastic bridge members 15 are bowed outwardly.

Figure 3:
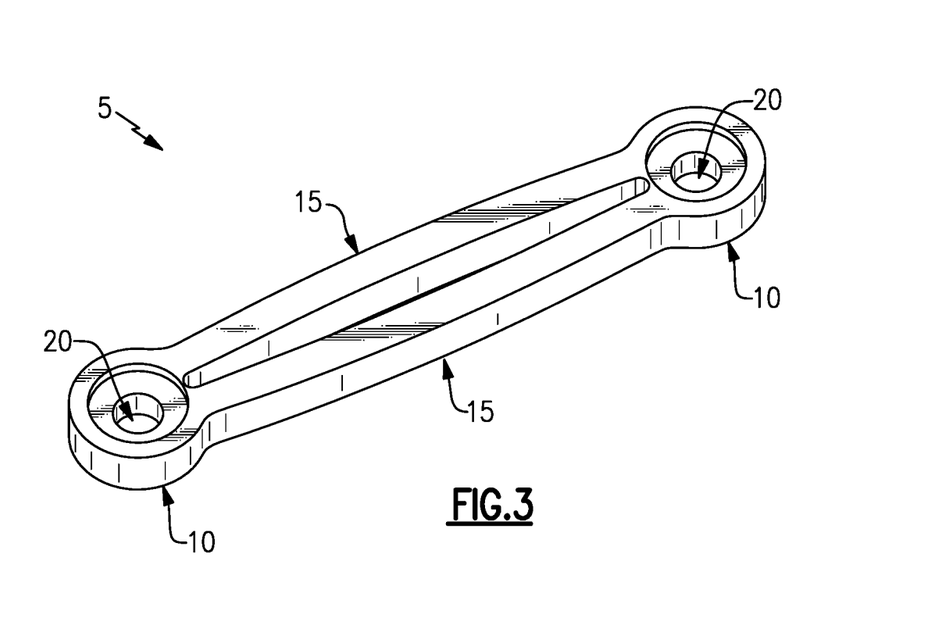
FIG. 3 is a schematic view of the compression plate elastically strained to a strained condition.
Figure 4:
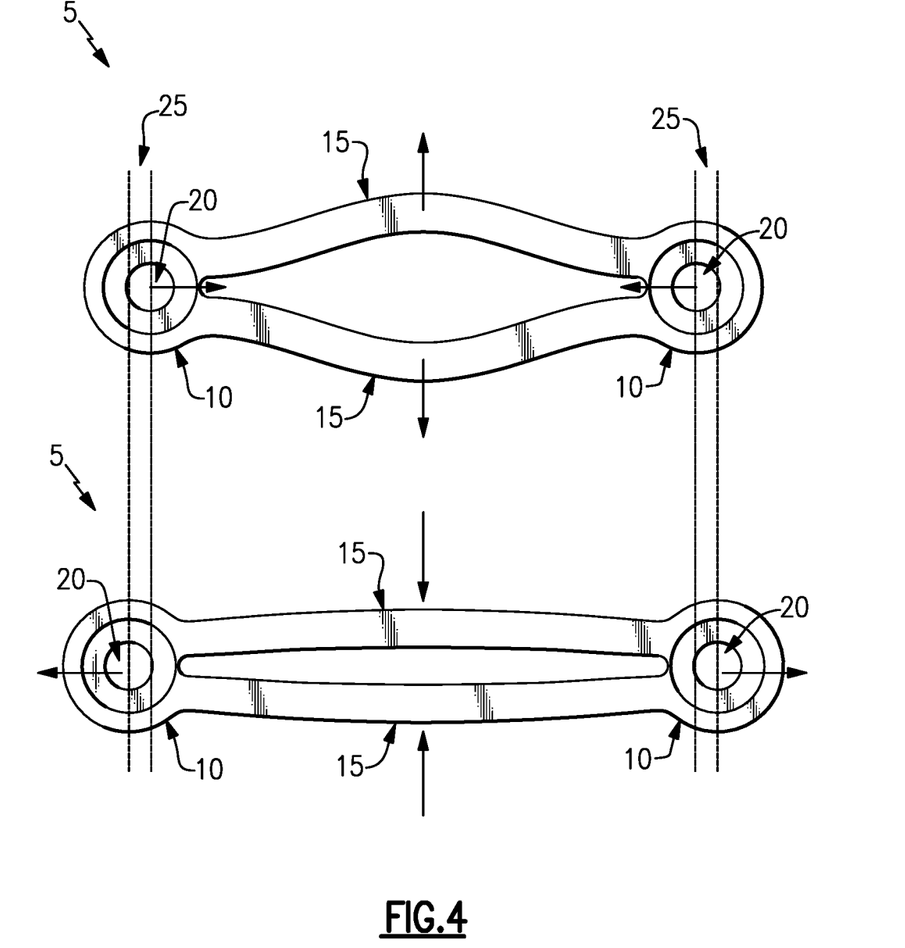
FIG. 4 is a schematic view of how the elastically strained compression plate foreshortens when a strain is removed.

As shown in FIG. 3, the compression plate 5 can be strained to be in the strained condition. Prior to implantation, the elastic bridge members 15 of the compression plate 5 are reversibly strained inwardly (i.e., bent laterally inwardly, as shown in FIG. 4), increasing the distance 25 between the opposing regions 10 (and therefore the openings 20) of the compression plate 5, resulting in the compression plate 5 being in the strained condition. The delivery device 12 can be used to strain elastic bridge members 15.

Returning to FIG. 1, while in the strained condition, the compression plate 5 is placed inside the body 14 of the delivery device 12 in the space 21 defined between the beam 18 of the body 14 and the beam 24 of the cover plate 22. Once the cover plate 22 is released and again located in the recess 55 of the body 14, an inner surface of the beam 18 of the body 14 presses against a side surface of one of the elastic bridge members 15 of the compression plate 5, and an inner surface of the beam 24 of the cover plate 22 presses against a side surface of the other elastic bridge members 15 of the compression plate 5, retaining the compression plate 5 in the strained condition.

Figure 5:
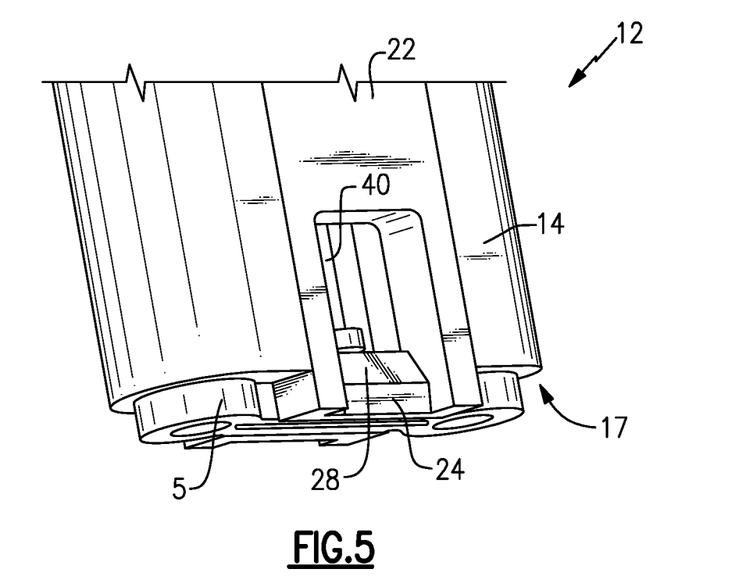
FIG. 5 illustrates another schematic perspective view of one side of the distal end of the body of the delivery device.
Figure 6:
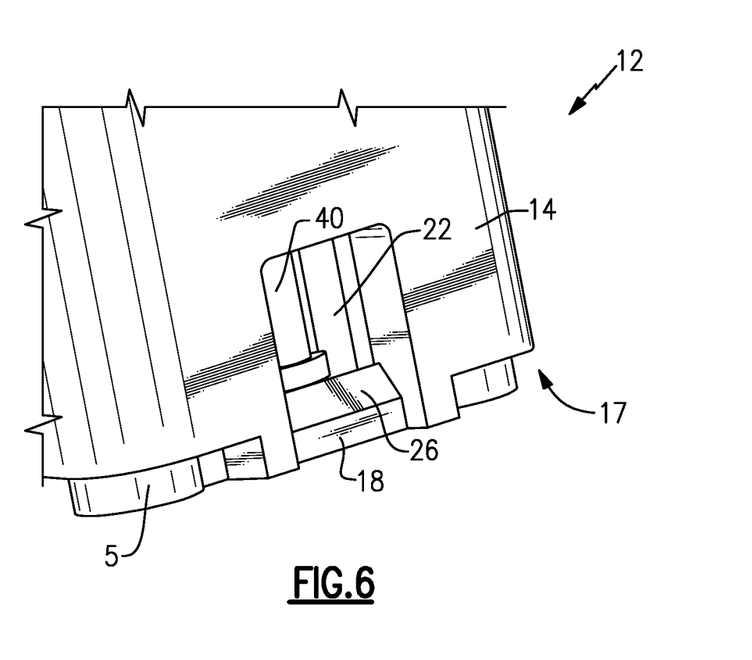
FIG. 6 illustrates another schematic perspective view of an opposing side of the distal end of the body of the delivery device.
Figure 7:
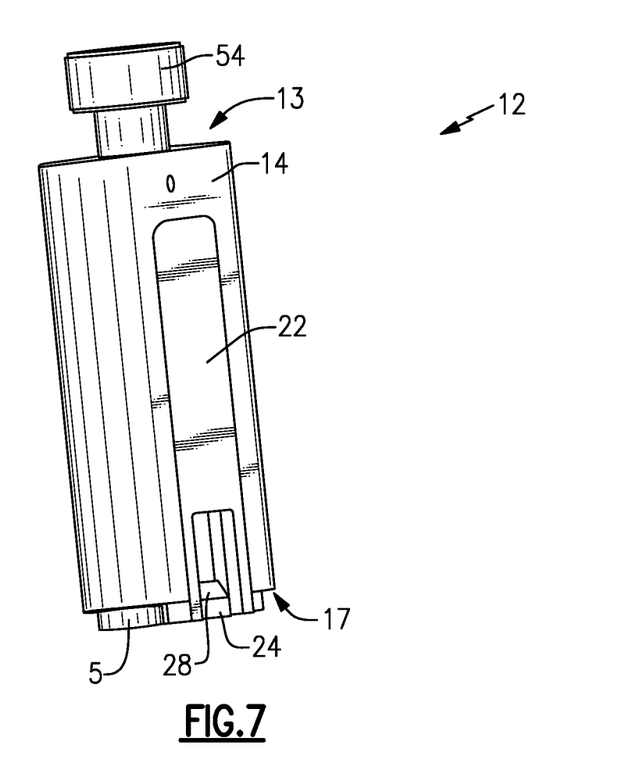
FIG. 7 illustrates a schematic perspective view of the delivery device.

As shown in FIGS. 5 and 6, an outer surface of the beam 18 of the body 14 includes a chamfered portion 26, and the outer surface of the beam 24 of the cover plate 22 includes a chamfered portion 28. The chamfered portion 26 and the chamfered portion 28 are located on a proximal portion of the beams 18 and 24, respectively As shown in FIG. 7, the cover plate 22 is attached to an upper region of the delivery device 12, allowing the cover plate 22 to articulate and cantilever outwardly at a distal region of the cover plate 22 that abuts the compression plate 5.

Figure 8:
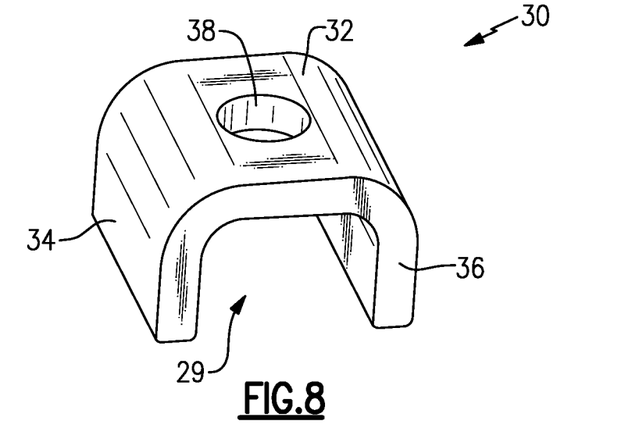
FIG. 8 illustrates a schematic view of a compression clip.

As shown in FIG. 8, a compression clip 30 is used to rigidly compress the compression plate 5 in the space 21 in the body 14 between the beam 24 of the body 14 and the beam 24 of the cover plate 22, maintaining the compression plate 5 in the strained condition and preventing the compression plate 5 from returning to the unstrained condition. The compression clip 30 includes an upper portion 32 with two side portions 34 and 36 that are substantially perpendicular to the upper portion 32. The upper portion 32 includes an opening 38. A space 29 is defined by the upper portion 32 and the two side portions 34 and 36 of the compression clip 30. The compression clip 30 also locks the distal region of the cover plate 22 in the recess 55 of the body 14.

Figure 9:
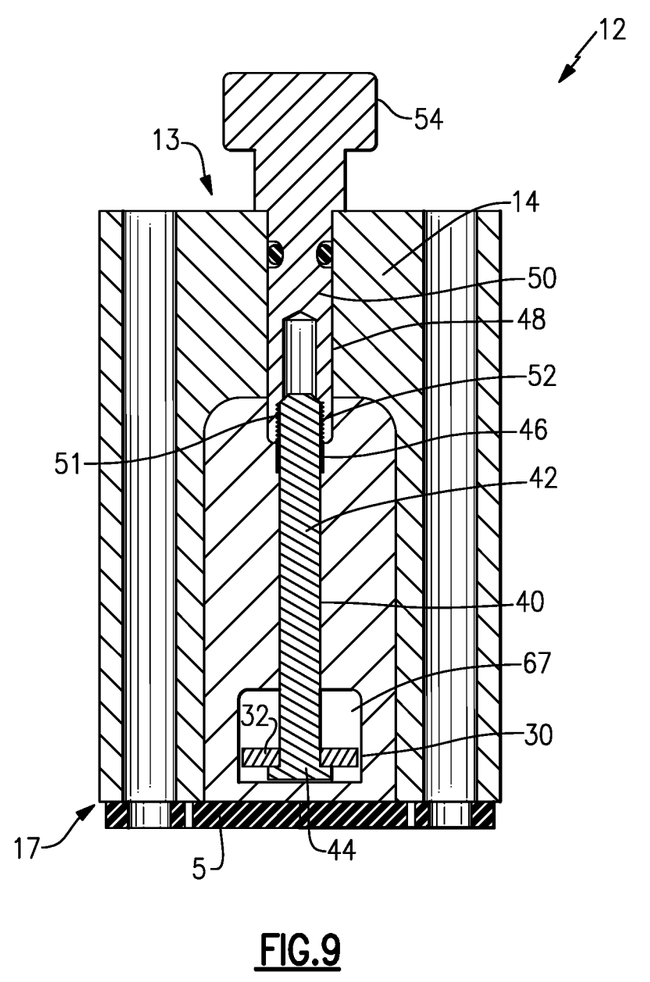
FIG. 9 illustrates a schematic cross-sectional view of the delivery device.

As shown in FIG. 9, a male threaded rod 40 includes a head 44 and a male stem 42 having male threads 46. The male threads 46 are located at one end of the male stem 42, and the head 44 is located at an opposing end of the male stem 42. The male stem 42 extends through the body 14 of the delivery device 12 and passes through the opening 38 in the compression clip 30 such that the head 44 of the male threaded rod 40 is located in the space 29 defined by the upper portion 32 and the two side portions 34 and 36 of the compression clip 30. The head 44 is located on an opposite side of the compression clip 30 from the male stem 42, linking the male threaded rod 40 and the compression clip 30.

A female threaded feature 48 includes a knob 54 and a female stem 50 having a passage 51 with female threads 52. The knob 54 is located at one end region of the female stem 50, and the female threads 52 are located at an opposing end region of the female stem 50.

The male threads 46 of the male threaded rod 40 engage the female threads 52 of the female threaded feature 48. The knob 54 is located on near the proximal end 13 of the delivery device 12. Turning the knob 54 (in one example, clockwise) causes the female threads 52 to engage the male threads 46, moving the male stem 42 of the male threaded rod 40 axially and therefore moving the head 44 of the male threaded rod 40 towards the proximal end 13 of the body 14. The head 44 contacts a lower surface of the upper portion 32, moving the compression clip 30 towards the proximal end 13 of the body 14 and away from the distal end 17 of the body 14 of the delivery device 12.

As the compression clip 30 moves into a cavity 67 of the body 14 of the delivery device 12, the two side portions 34 and 36 of the compression clip 30 ride on the chamfered portion 26 and 28 of the body 14 and the cover plate 22, respectively. Once the compression clip 30 is spaced from the beams 18 and 24 of the body 14 and the cover plate 22, respectively, the distal region of the cover plate 22 is no longer locked in the recess 55 of the body 14 by the compression clip 30. The cover plate 22 can slowly and controllably move away from the compression plate 5, allowing the compression plate 5 to release from the delivery device 12.

Removal of the induced strain on the compression plate 5 applied by the delivery device 12 results in the compression plate 5 attempting to return to the original unstrained condition, generating a compressive load on the bone (i.e., through the elastic bridge members 15, the openings 20, and the threaded fixation screws 120) and maintaining a compressive load on the bone for a prolonged period of time during healing.

FIGS. 10a to 14b show a method for treating a fracture 300 formed between two bone fragments 305 using the compression plate 5.

Figures 10A, 10B, 11A, 11B, 12A, 12B:
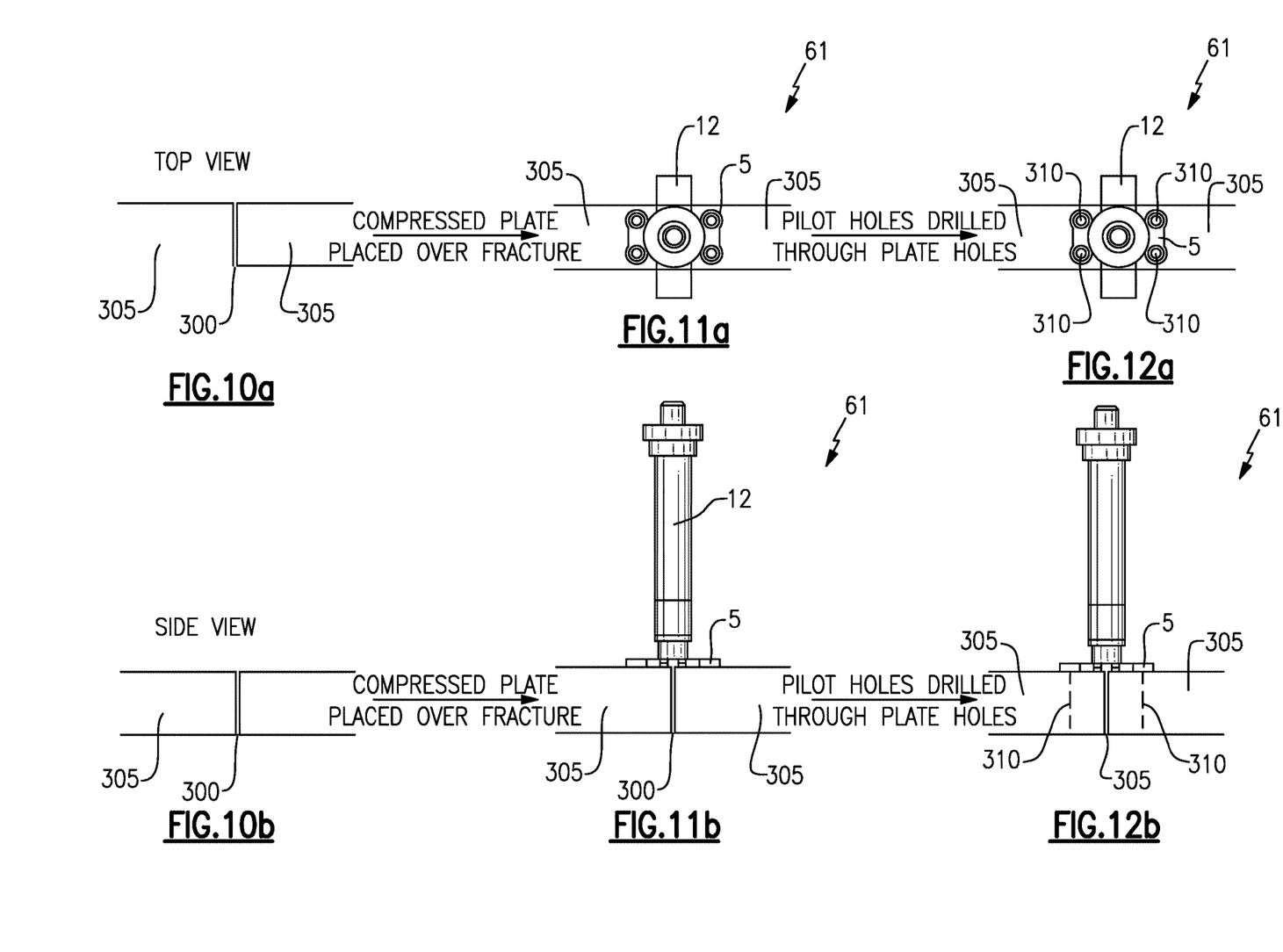
FIG. 10a shows a top view of the fracture line between two bone fragments.
FIG. 10b shows a side view of the fracture line between the two bone fragments.
FIG. 11a shows a top view of the delivery device with the compression plate positioned over the fracture line.
FIG. 11b shows a side view the delivery device with the compression plate positioned over the fracture line.
FIG. 12a shows a top view of holes being drilled in the bone fragments through openings in the compression plate.
FIG. 12b shows a top view of the holes being drilled in the bone fragments through the openings in the compression plate.
Figure 13A:
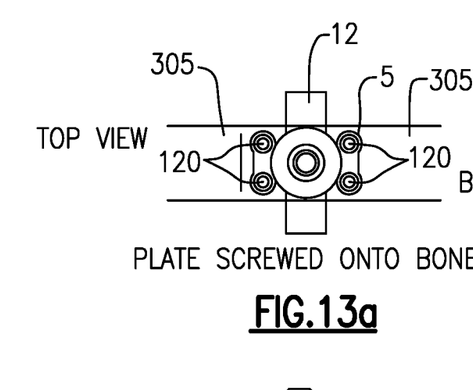
FIG. 13a shows a top view of threaded fasteners being drilled in the openings in the compression plate.
Figure 13B:
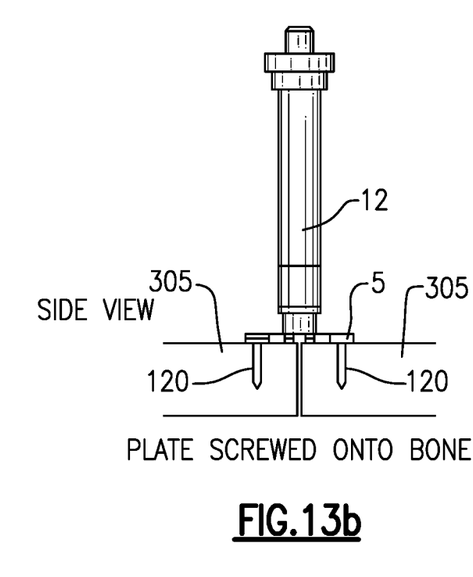
FIG. 13b shows a top view of the threaded fasteners being drilled in the openings in the compression plate.
Figure 14A:
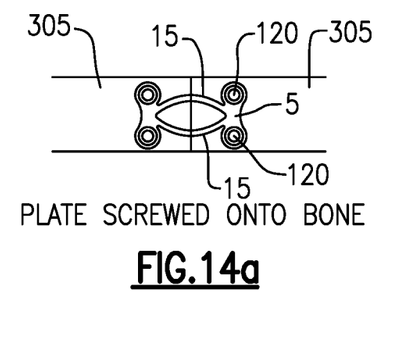
FIG. 14a shows a top view of the compression plate attached to the bone fragments.
Figure 14B:
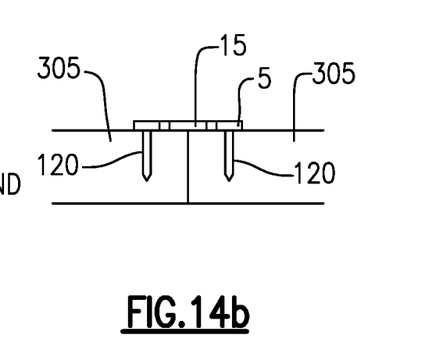
FIG. 14b shows a top view of the compression plate attached to the bone fragments.

FIGS. 10a and 10b show a fracture line 300 between bone fragments 305. When the compression plate 5 is loaded into the delivery device 12, the elastic bridge members 15 of the compression plate 5 are biased to the strained condition so that they are near-parallel (or at least more parallel). As shown in FIGS. 11a and 11b, the strained compression plate 5 is then placed over the fracture line 300. Holes 310 are drilled into the bone fragments 305 through the openings 20 of the compression plate 5, as shown in FIGS. 12a and 12b. As shown in FIGS. 13a and 13b, the threaded fixation screws 120 are advanced through the holes 310 drilled into the bone fragments 305 through the openings 20 of the compression plate 5, fixing the compression plate 5 to the bone fragments 305. As shown in FIGS. 14a and 14b, the delivery device 12 is then removed, leaving the compression plate 5 attached to the bone fragments 305. The compression plate 5 attempts to regain its original unstrained shape shown in FIG. 2, thereby generating and maintaining compression across the fracture line 300 between the bone fragments 305.

Figure 15:
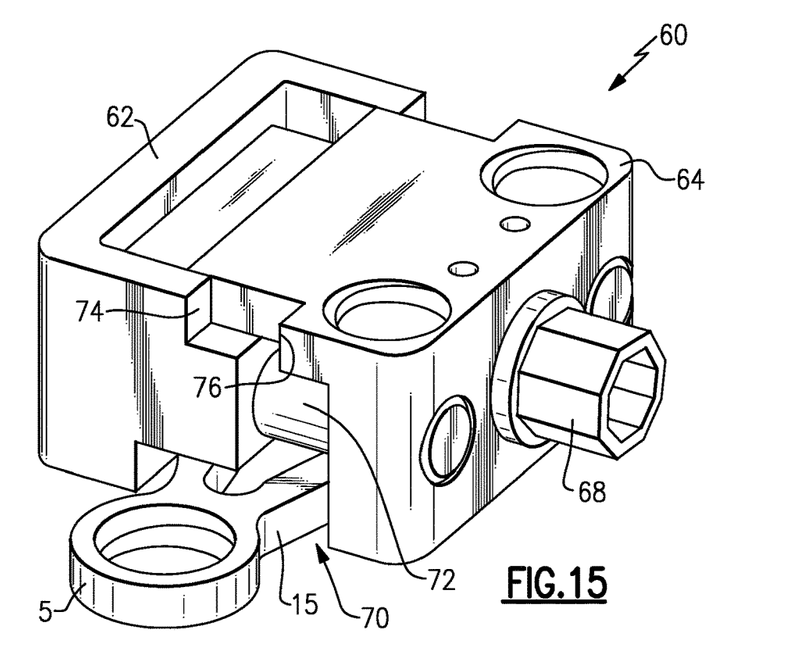
FIG. 15 shows an upper perspective view of another delivery device.
Figure 16:
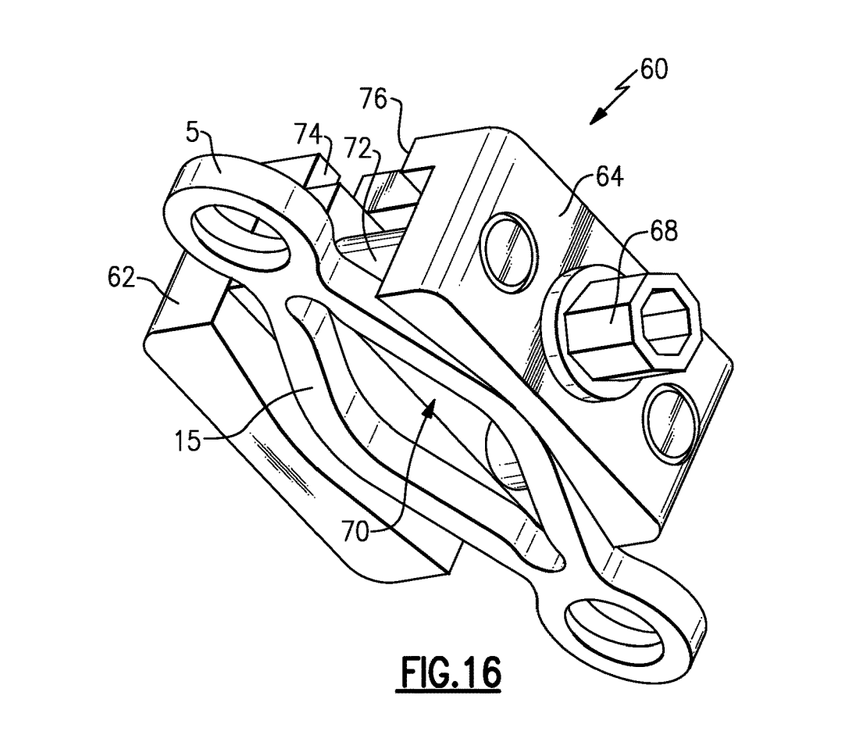
FIG. 16 shows a lower perspective view of the another delivery device.

FIGS. 15 and 16 show another example delivery device 60. The delivery device 60 includes a first portion 62 and a second portion 64. Each portion 62 and 64 include an aperture (not shown) that receives a threaded fastener 68. The delivery device 60 also includes two rods 72 that keep the first portion 62 and the second portion 64 aligned relative to each other. The first portion 62 and the second portion 64 move relative to the two rods 72.

A recess 70 is defined between the first portion 62 and the second portion 64 that receives a compression plate 5. The threaded fastener 68 can be turned in a first direction to move the first portion 62 and the second portion 64 towards each other and reduce a width W of the recess 70. The threaded fastener 68 can be turned in an opposing second direction to move the first portion 62 and the second portion 64 away from each other and increase the width W of the recess 70.

Figure 17:
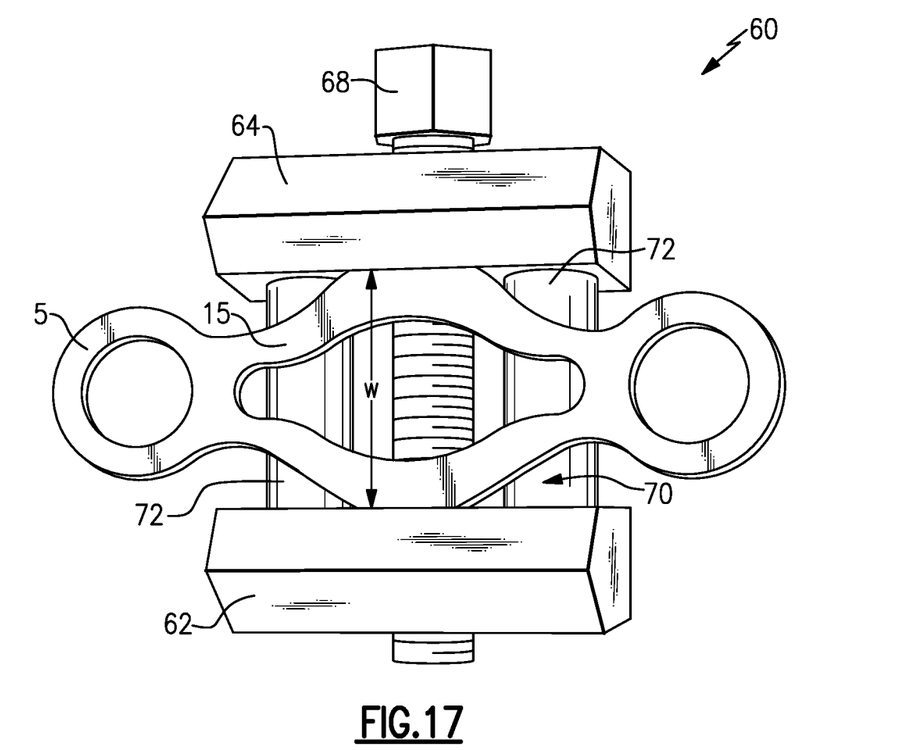
FIG. 17 shows a lower view of the another delivery device.
Figure 18:
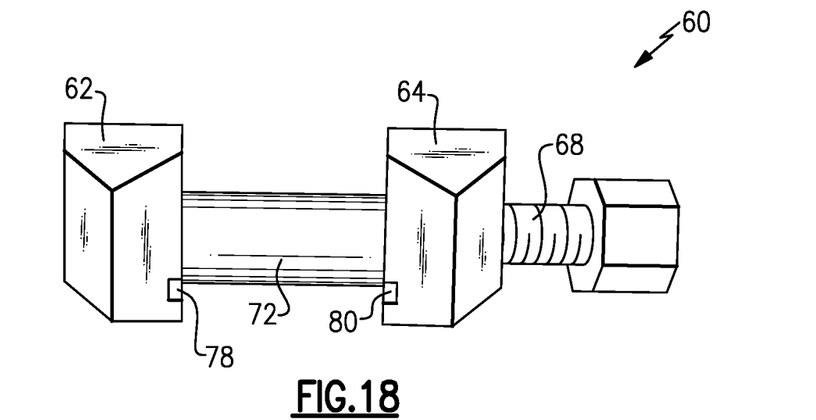
FIG. 18 shows a side view of the another delivery device.

FIG. 17 shows a compression plate 5 positioned in the recess 70 of the delivery device 60 in the unstrained condition. Also, as shown in FIG. 18, the first portion 62 and the second portion 64 each include a groove 78 and 80, respectively, that receive a portion of the bridge members 15 of the compression plate 5 to align the compression plate 5 during straining.

As the threaded fastener 68 is turned in the first direction, the width W of the recess 70 decreases, straining the compression plate 5 towards the strained condition such that the bridge members 15 are near parallel to each other. In this position, the compression plate 5 will be in the strained condition and ready for attachment to the bone fragments. As the first portion 62 moves towards the second portion 64, a surface 74 of the first portion 62 eventually engages a surface 76 of the second portion 64. The surfaces 74 and 76 act as a stop to prevent further movement of the portions 62 and 64.

Once the compression plate 5 is attached to the bone fragments, the threaded fastener 68 can be turned in the second direction to move the portions 72 and 74 away from each other, increasing the width W of the recess 70 to allow for removal of the compression plate 5 from the delivery device 60.

In one example, a delivery device delivers a compression plate to a fracture line in a bone. The delivery device includes a body that retains a compression plate in a strained condition. The body includes a proximal end, a distal end, a first beam, a cavity, and a recess. A cover plate is attached at the proximal end of the body and moveable relative to the body. The cover plate includes a second beam. The cover plate is received in the recess of the body. A space is defined between the first beam and the second beam that receives the compression plate. A compression clip retains the compression plate in the space in the strained condition and prevents the compression plate from returning to an unstrained condition. The compression clip includes an upper portion and two side portions that are substantially perpendicular to the upper portion. The upper portion includes an opening, and the cover plate can move relative to the compression plate at the distal end of the body to allow the compression plate to release from the delivery device. A male threaded rod includes a head and a male stem having male threads. The male threads are located at one end region of the male stem and the head is located at an opposing end region of the male stem. The head is located proximate to the distal end of the body and in an area defined by the upper portion and the two side portions of the compression clip. The male stem extends from the head, through the opening of the compression clip, and the through the body of the delivery device. A female threaded feature includes a knob and a female stem having a passage with female threads. The knob is located at one end region of the female stem. The female threads are located at an opposing end region of the female stem. The male threads of the male threaded rod engage the female threads of the female threaded feature. Rotation of the knob moves the male stem and thereby the head axially towards the proximal end of the body. The head contacts the upper portion of the compression clip to move the compression clip towards the proximal end of the body of the delivery device to release the compression clip. When the compression clip is received in a cavity of the body, the cover plate can move away from the compression plate at the distal end of the body to allow the compression plate to release from the delivery device.

In another example, a delivery device delivers a compression plate to a fracture line in a bone. The delivery device includes a body that retains a compression plate in a strained condition. The body includes a proximal end, a distal end, and a first beam. A cover plate is attached to and moveable relative to the body. The cover plate includes a second beam. A space is defined between the first beam and the second beam that receives the compression plate. A compression clip retains the compression plate in the space.

In another embodiment according to any of the previous embodiments, the compression clip includes an upper portion and two side portions that are substantially perpendicular to the upper portion. The upper portion includes an opening.

In another embodiment according to any of the previous embodiments, the first beam includes a first chamfered portion and the second beam includes a second chamfered portion. The first chamfered portion and the second chamfered portion are located on a proximal portion of the first beam and the second beam, respectively.

In another embodiment according to any of the previous embodiments, the cover plate is attached near or at the proximal end of the body and, when the compression clip is received in a cavity of the body, the cover plate can move away from the compression plate at the distal end of the body to allow the compression plate to release from the delivery device.

In another embodiment according to any of the previous embodiments, the delivery device includes a male threaded rod and a female threaded feature. The male threaded rod includes a head and a male stem having male threads. The male threads are located at one end of the male stem and the head is located at an opposing end of the male stem. The head is located proximate to the distal end of the body and in an area defined by the upper portion and the two side portions of the compression clip. The male stem extends from the head, through the opening of the compression clip, and the through the body of the delivery device. The female threaded feature includes a knob and a female stem having a passage with female threads. The knob is located at one end region of the female stem, and the female threads are located at an opposing end region of the female stem.

In another embodiment according to any of the previous embodiments, the male threads of the male threaded rod engage the female threads of the female threaded feature. Rotation of the knob moves the male stem and thereby the head axially towards the proximal end of the body. The head contacts the upper portion of the compression clip to move the compression clip towards the proximal end of the body of the delivery device to release the compression clip.

In another embodiment according to any of the previous embodiments, when the compression clip is received in a cavity of the body, the cover plate can move away from the compression plate at the distal end of the body to release the compression plate from the delivery device In another embodiment according to any of the previous embodiments, the compression clip locks the cover plate relative to the body.

In another embodiment according to any of the previous embodiments, the first beam and the second beam are at the distal end of the body.

In another embodiment according to any of the previous embodiments, the body includes a recess, and the cover plate is received in the recess of the body.

In another embodiment according to any of the previous embodiments, the compression plate includes an elastic bridge member disposed on both sides of a center line. First and second opposing regions each comprise an opening and are connected by the elastic bridge member. The elastic bridge member is bowed outwardly relative to the center line when in an unstrained condition. The compression plate has a more linear configuration when the compression plate is in the strained condition.

In another embodiment according to any of the previous embodiments, the openings in the first and second opposing regions are separated by a first distance when the compression plate is in the unstrained condition. The openings in the first and second opposing regions are separated by a second distance when the compression plate is in the strained condition, and the second distance is greater than the first distance.

In another example, a method of repairing a fracture line in a bone includes loading a compression plate between a body and a cover plate of a delivery device to position the compression plate in the strained condition. The compression plate is placed over the fracture line. A compression clip is axially moved away from the compression plate. The cover plate is released from the body to allow the cover plate to move relative to the body. The compression plate is released from the delivery device.

In another embodiment according to any of the previous embodiments, the method includes drilling holes through openings in the compression plate. Threaded fasteners are advanced through the openings and into the bone fragments to secure the compression plate to the bone fragments. The delivery device is removed. Compression is generated and maintained across the fracture line as the compression plate tries to return to the unstrained condition.

In another example, a delivery device delivers a compression plate to a fracture line in a bone. The delivery device includes a body that retains a compression plate in a recess in a strained condition. The body includes a first portion and a second portion defining the recess therebetween. The first portion and the second portion are moveable relative to each other to change a dimension of the recess to compress the compression plate from an unstrained condition to the strained condition. A threaded fastener is turned to move the first portion and the second portion towards each other and reduce the dimension of the recess and compression the compression plate from the unstrained condition to the strained condition. An alignment feature that aligns the first portion and the second portion relative to each other.

In another embodiment according to any of the previous embodiments, the first portion and the second portion each include a groove to receive a portion of the compression plate.

In another embodiment according to any of the previous embodiments, the first portion and the second portion each include a surface that acts as a stop to prevent movement of the first portion and the second portion towards each other.

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A delivery device for delivering a compression plate to a fracture line in a bone, the delivery device comprising:

a body that retains a compression plate in a strained condition, the body including a proximal end, a distal end, a first beam, a cavity, and a recess;

a cover plate attached at the proximal end of the body and moveable relative to the body, the cover plate including a second beam, wherein the cover plate is received in the recess of the body;

a space defined between the first beam and the second beam that receives the compression plate;

a compression clip that retains the compression plate in the space in the strained condition and prevents the compression plate from returning to an unstrained condition, the compression clip including an upper portion and two side portions that are substantially perpendicular to the upper portion, the upper portion including an opening, and the cover plate can move relative to the compression plate at the distal end of the body to allow the compression plate to release from the delivery device;

a male threaded rod including a head and a male stem having male threads, wherein the male threads are located at one end region of the male stem and the head is located at an opposing end region of the male stem, and the head is located proximate to the distal end of the body and in an area defined by the upper portion and the two side portions of the compression clip, and the male stem extends from the head, through the opening of the compression clip, and the through the body of the delivery device; and a female threaded feature including a knob and a female stem having a passage with female threads, wherein the knob is located at one end region of the female stem, and the female threads are located at an opposing end region of the female stem, wherein the male threads of the male threaded rod engage the female threads of the female threaded feature, and rotation of the knob moves the male stem and thereby the head axially towards the proximal end of the body, and the head contacts the upper portion of the compression clip to move the compression clip towards the proximal end of the body of the delivery device to release the compression clip, and wherein, when the compression clip is received in a cavity of the body, the cover plate can move away from the compression plate at the distal end of the body to allow the compression plate to release from the delivery device.

2. A delivery device for delivering a compression plate to a fracture line in a bone, the delivery device comprising:

a body that retains a compression plate in a strained condition, the body including a proximal end, a distal end, and a first beam;

a cover plate attached to and moveable relative to the body, the cover plate including a second beam;

a space defined between the first beam and the second beam that receives the compression plate; and a compression clip that retains the compression plate in the space.

3. The delivery device as recited in claim 2 wherein the compression clip includes an upper portion and two side portions that are substantially perpendicular to the upper portion, wherein the upper portion includes an opening.

4. The delivery device as recited in claim 3 wherein the first beam includes a first chamfered portion and the second beam includes a second chamfered portion, wherein the first chamfered portion and the second chamfered portion are located on a proximal portion of the first beam and the second beam, respectively.

5. The delivery device as recited in claim 3 wherein the cover plate is attached near or at the proximal end of the body and, when the compression clip is received in a cavity of the body, the cover plate can move away from the compression plate at the distal end of the body to allow the compression plate to release from the delivery device.

6. The delivery device as recited in claim 3 including a male threaded rod and a female threaded feature, wherein the male threaded rod includes a head and a male stem having male threads, the male threads are located at one end of the male stem and the head is located at an opposing end of the male stem, and the head is located proximate to the distal end of the body and in an area defined by the upper portion and the two side portions of the compression clip, and the male stem extends from the head, through the opening of the compression clip, and the through the body of the delivery device, and wherein the female threaded feature includes a knob and a female stem having a passage with female threads, wherein the knob is located at one end region of the female stem, and the female threads are located at an opposing end region of the female stem.

7. The delivery device as recited in claim 6 wherein the male threads of the male threaded rod engage the female threads of the female threaded feature, and rotation of the knob moves the male stem and thereby the head axially towards the proximal end of the body, and the head contacts the upper portion of the compression clip to move the compression clip towards the proximal end of the body of the delivery device to release the compression clip.

8. The delivery device as recited in claim 2 wherein, when the compression clip is received in a cavity of the body, the cover plate can move away from the compression plate at the distal end of the body to release the compression plate from the delivery device.

9. The delivery device as recited in claim 2 wherein the compression clip locks the cover plate relative to the body.

10. The delivery device as recited in claim 2 wherein the first beam and the second beam are at the distal end of the body.

11. The delivery device as recited in claim 2 wherein the body includes a recess, and the cover plate is received in the recess of the body.

12. The delivery device according to claim 2 wherein the compression plate comprises an elastic bridge member disposed on both sides of a center line, first and second opposing regions that each comprise an opening and are connected by the elastic bridge member, and the elastic bridge member is bowed outwardly relative to the center line when in an unstrained condition, and the compression plate has a more linear configuration when the compression plate is in the strained condition.

13. The delivery device according to claim 12 wherein the openings in the first and second opposing regions are separated by a first distance when the compression plate is in the unstrained condition, and the openings in the first and second opposing regions are separated by a second distance when the compression plate is in the strained condition, and the second distance is greater than the first distance.

* * * * *